US00PP17335P2

(12) United States Plant Patent
Heil

(10) Patent No.: US PP17,335 P2
(45) Date of Patent: Jan. 2, 2007

(54) CARNATION PLANT NAMED 'MARGARITA'

(50) Latin Name: *Dianthus caryophyllus*
Varietal Denomination: Margarita

(75) Inventor: Johan Edwin Heil, Aalsmeer (NL)

(73) Assignee: P. Kooij & Zonen B.V., Aalsmeer (NL)

( * ) Notice: Subject to any disclaimer, the term of this patent is extended or adjusted under 35 U.S.C. 154(b) by 79 days.

(21) Appl. No.: 11/073,467

(22) Filed: Mar. 5, 2005

(51) Int. Cl.
*A01H 5/00* (2006.01)

(52) U.S. Cl. ..... Plt./273

(58) Field of Classification Search ..... Plt./273
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of Carnation plant named 'Margarita', characterized by its compact, upright and rounded plant habit; freely basal branching habit; freely flowering habit; and red purple and white bi-colored flowers.

1 Drawing Sheet

Botanical designation: *Dianthus caryophyllus.*
Cultivar denomination: 'Margarita'.

BACKGROUND OF THE INVENTION

The present invention relates to a new and distinct cultivar of potted Carnation plant, botanically known as *Dianthus caryophyllus* and hereinafter referred to by the cultivar name Margarita.

The new Carnation is a product of a planned breeding program conducted by the Inventor in Aalsmeer, The Netherlands. The objective of the breeding program is to develop new compact Carnation cultivars suitable for container production with attractive flower coloration.

The new Carnation originated from a cross-pollination made by the Inventor of the *Dianthus caryophyllus* cultivar Kowipa, disclosed in U.S. Plant Pat. No. 11,808, as the female, or seed, parent with a proprietary selection of *Dianthus caryophyllus* identified as code number 996090-06, not patented, as the male, or pollen, parent. The cultivar Margarita was discovered and selected by the Inventor as a flowering plant within the progeny of the stated cross-pollination in a controlled environment in Aalsmeer, The Netherlands, in 2000.

Asexual reproduction of the new cultivar by terminal cuttings at Aalsmeer, The Netherlands, has shown that the unique features of this new Carnation are stable and reproduced true to type in successive generations of asexual reproduction.

SUMMARY OF THE INVENTION

The cultivar Margarita has not been observed under all possible environmental conditions. The phenotype may vary somewhat with variations in environment such as temperature and light intensity without, however, any variance in genotype.

The following traits have been repeatedly observed and are determined to be the unique characteristics of 'Margarita'. These characteristics in combination distinguish 'Margarita' as a new and distinct cultivar:

1. Compact, upright and rounded plant habit.
2. Freely basal branching habit.
3. Freely flowering habit.
4. Red purple and white bi-colored flowers.

Compared to plants of the female parent, the cultivar Kowipa, plants of the new Carnation are taller and broader, have longer leaves, have fewer petals per flower and have darker-colored flowers. Compared to plants of the male parent selection, plants of the new Carnation are more compact and have lighter-colored flowers.

Plants of the new Carnation can be compared to plants of the cultivar Pink Surprise, not patented. In side-by-side comparisons conducted in Aalsmeer, The Netherlands, plants of the new Carnation and the cultivar Pink Surprise differed in the following characteristics:

1. Plants of the new Carnation were more freely flowering than plants of the cultivar Pink Surprise.
2. Plants of the new Carnation and the cultivar Pink Surprise differed in flower coloration.

BRIEF DESCRIPTION OF THE PHOTOGRAPH

The accompanying colored photograph illustrates the overall appearance of the new Carnation, showing the colors as true as it is reasonably possible to obtain in colored reproductions of this type. Colors in the photograph may differ slightly from the color values cited in the detailed botanical description which accurately describe the colors of the new Carnation.

The photograph comprises a top perspective view of a typical flowering plant of 'Margarita' grown in a container.

DETAILED BOTANICAL DESCRIPTION

In the following description, color references are made to The Royal Horticultural Society Colour Chart, 1995 edition, except where general terms of ordinary dictionary significance are used. The aforementioned photographs, following observations and measurements describe plants grown in Aalsmeer, The Netherlands in a glass-covered greenhouse. During the production of the plants, day temperatures were about 15° C. and night temperatures were about 8° C. Rooted young plants were planted in 10-cm containers and pinched once. The photographs and the description were taken about five months after planting.

Botanical classification: *Dianthus caryophyllus* cultivar Margarita.

Parentage:

*Female, or seed, parent.*—*Dianthus caryophyllus* cultivar Kowipa, disclosed in U.S. Plant Pat. No. 11,808.

*Male, or pollen, parent.*—Proprietary selection of *Dianthus caryophyllus* identified as code number 996090-06, not patented.

Propagation:

*Type.*—By cuttings.

*Time to initiate roots, summer.*—About 8 days at 25° C.

*Time to initiate roots, winter.*—About 13 days at 18° C.

*Time to produce a rooted young plant, summer.*—About 20 days at 25° C.

*Time to produce a rooted young plant, winter.*—About 30 days at 18° C.

*Root description.*—Fine, fibrous.

*Rooting habit.*—Freely branching.

Plant description:

*Plant habit.*—Compact, upright and rounded plant habit.

*Growth habit.*—Freely basal branching; about four lateral branches per plant. Moderately vigorous.

*Plant height.*—About 20 cm.

*Plant width.*—About 25 cm.

*Lateral branch description.*—Length: About 10 cm. Diameter: About 2.5 mm. Internode length: About 7 mm. Aspect: Upright. Strength: Strong. Texture: Glabrous; smooth. Color: 145C.

*Foliage description.*—Arrangement: Leaves opposite; simple; symmetrical; abundant; sessile and decurrent. Length: About 15 cm. Width: About 6 mm. Shape: Linear. Apex: Acute. Margin: Entire. Texture, upper and lower surfaces: Glabrous; smooth. Venation pattern: Parallel, linear. Color: Developing foliage, upper and lower surfaces: 137C. Fully expanded foliage, upper and lower surfaces: 137C; venation, 137B.

Flower description:

*Appearance.*—Rotate flowers that face mostly upright. Freely flowering habit, about ten open flowers and flower buds per lateral branch.

*Flowering response.*—Plants flower during the summer in The Netherlands; during this period, flowering is continuous.

*Postproduction longevity.*—Flowers last about one week on the plant. Flowers persistent.

*Fragrance.*—Moderate; clove-like.

*Flower size.*—Diameter: About 3.5 cm. Depth (height): About 3 cm.

*Flower buds.*—Length: About 1.7 cm. Diameter: About 7 mm. Shape: Ovoid. Color: 146B.

*Petals.*—Quantity/arrangment: About nine per flower in about two whorls. Length: About 4 cm. Width: About 1.8 cm. Shape: Flabellate. Apex: Rounded, praemorse. Base: Attenuate. Margin: Serrate. Texture, upper and lower surfaces: Smooth, glabrous. Color: When opening and fully opened, upper surface: 59A, towards the margin, 155D; color becoming closer to 64B with development. When opening and fully opened, lower surface: 63B.

*Sepals.*—Quantity/arrangement: Five per flower fused into a calyx tube. Calyx length: About 2.4 cm. Calyx diameter: About 1 cm. Shape: Elliptic. Apex: Acute. Texture, upper and lower surfaces: Smooth, glabrous. Color, upper surface: 146B. Color, lower surface: 139C.

*Peduncles.*—Length: About 1 mm. Diameter: About 1 mm. Aspect: Upright. Strength: Moderately strong. Texture: Smooth; glabrous. Color: 145C.

*Reproductive organs.*—Androecium: Stamen number: About six. Filament color: 155D. Anther length: About 2 mm. Anther shape: Roughly oblong. Anther color: Close to 155D. Pollen: Moderate. Gynoecium: Pistil quantity: Two. Stigma color: 64D. Style length: About 3.1 cm. Style color: 155D. Ovary color: 145A.

*Seed.*—Length: About 3 mm. Diameter: About 2 mm. Color: 200A.

Disease/pest resistance: Plants of the new Carnation have not been observed to be resistant to pathogens nor pests common to Carnation.

It is claimed:

1. A new and distinct cultivar of Carnation plant named 'Margarita', as illustrated and described.

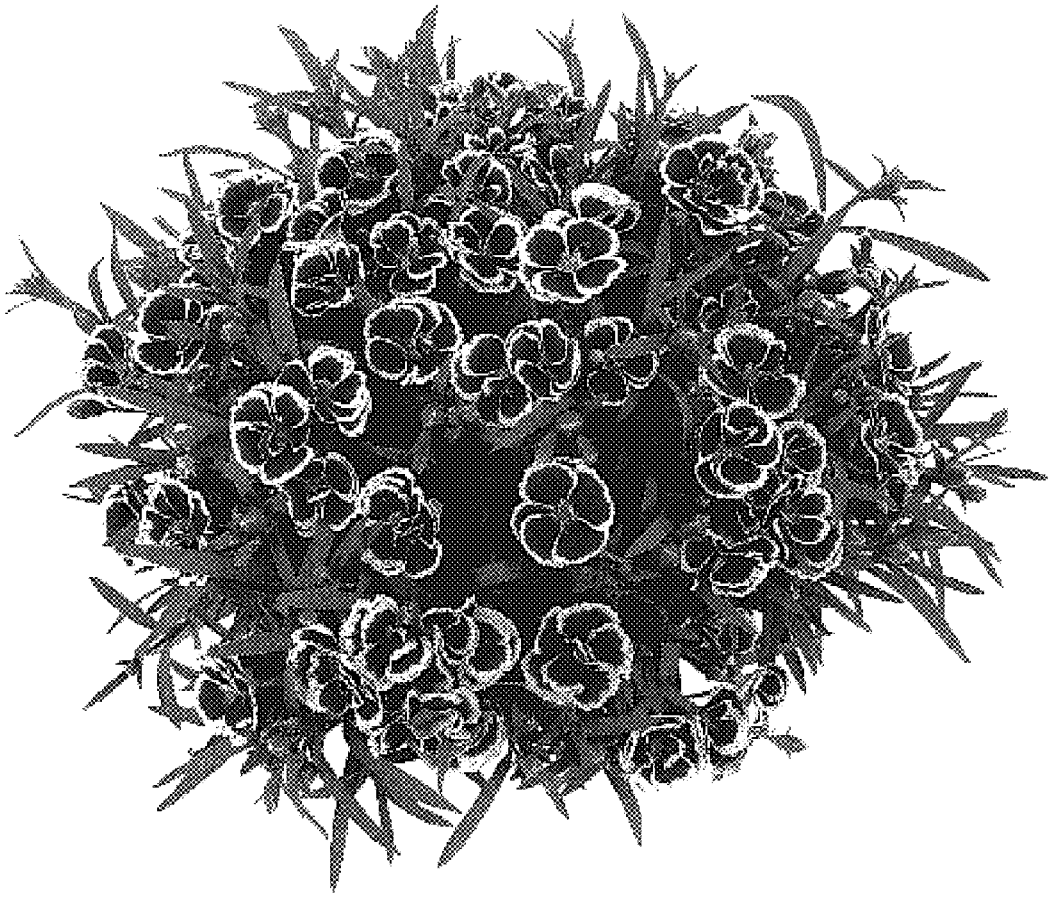

* * * * *